(12) United States Patent
Giordano

(10) Patent No.: US 11,484,344 B2
(45) Date of Patent: Nov. 1, 2022

(54) LOCKING DEVICE FOR AN EXTERNAL FIXATOR FOR BONE FRACTURE

(71) Applicant: NEWPHARM S.R.L., Santa Giustina in Colle (IT)

(72) Inventor: Raffaele Giordano, Romano di Lombardia (IT)

(73) Assignee: NEWPHARM S.R.L., Santa Giustina in Colle (IT)

( * ) Notice: Subject to any disclaimer, the term of this patent is extended or adjusted under 35 U.S.C. 154(b) by 0 days.

(21) Appl. No.: 17/297,169

(22) PCT Filed: Dec. 19, 2018

(86) PCT No.: PCT/IB2018/060340
§ 371 (c)(1),
(2) Date: May 26, 2021

(87) PCT Pub. No.: WO2020/128582
PCT Pub. Date: Jun. 25, 2020

(65) Prior Publication Data
US 2022/0022918 A1    Jan. 27, 2022

(51) Int. Cl.
*A61B 17/64* (2006.01)
(52) U.S. Cl.
CPC ............................. *A61B 17/6483* (2013.01)
(58) Field of Classification Search
CPC .......... A61B 17/62; A61B 17/64–6491; Y10T 403/7182; Y10T 403/7188; Y10T 403/53
See application file for complete search history.

(56) References Cited

U.S. PATENT DOCUMENTS

| | | | | |
|---|---|---|---|---|
| 5,797,908 A * | 8/1998 | Meyers | ............. | A61B 17/6483 606/54 |
| 5,863,292 A | 1/1999 | Tosic | | |
| 5,928,230 A | 7/1999 | Tosic | | |
| 7,491,008 B2 * | 2/2009 | Thomke | ............. | A61B 17/645 403/316 |
| 2004/0073212 A1 * | 4/2004 | Kim | ....................... | A61B 17/62 606/56 |
| 2007/0038217 A1 * | 2/2007 | Brown | ............. | A61B 17/6466 606/57 |
| 2009/0326532 A1 * | 12/2009 | Schulze | ............ | A61B 17/6466 606/56 |
| 2012/0209264 A1 * | 8/2012 | Zandona | ............ | A61B 17/6466 606/54 |
| 2014/0114310 A1 | 4/2014 | Leyton Virgen et al. | | |
| 2018/0132897 A1 * | 5/2018 | Shiner | ................ | A61B 17/6466 |

(Continued)

*Primary Examiner* — Lynnsy M Summitt
(74) *Attorney, Agent, or Firm* — Pearne & Gordon LLP

(57) ABSTRACT

A locking device (5) of a bone screw (3) for an external fixator (1) for bone fractures is described herein, wherein the external fixator (1) comprises at least one support pin (202). The locking device (5) comprises a locking element (501) of the bone screw (3); a locking pin (502), which is configured to support the locking element (501), the locking element (501) being configured to rotate around the blocking pin in a bone screw positioning step; a coupling element (503), which is provided with a respective coupling seat (503b) configured to receive the support pin (202) by snap-fit coupling and to allow, during the bone screw (3) positioning step, a rotation of the locking device (5) around the support pin (202) and a sliding of the locking device (5) along the support pin.

12 Claims, 10 Drawing Sheets

(56) References Cited

U.S. PATENT DOCUMENTS

| | | | |
|---|---|---|---|
| 2018/0289403 A1* | 10/2018 | Shoshtaev | A61B 17/7049 |
| 2019/0110814 A1* | 4/2019 | Nemovicher | A61B 17/645 |
| 2020/0069349 A1* | 3/2020 | Lavi | A61B 17/846 |

* cited by examiner

LOCKING DEVICE FOR AN EXTERNAL FIXATOR FOR BONE FRACTURE

TECHNICAL FIELD

The present invention relates to a locking device for an external fixator for bone fractures.

In particular, the present invention relates to a device for locking a bone screw, whose orientation and position in the external fixator determines the position and orientation of each bone screw with respect to a main direction of extension of the bone to be strengthened.

STATE OF THE ART

Very often different structures are involved in bone fractures, including tendons, bones and blood vessels in contact with the bone: all these structures must be treated in an optimal way to ensure the good recovery of functionality.

In the orthopaedic medical field, different types of external fixators for bone fractures are known which involve a reduction of the surgical impact on the patient with numerous advantages such as early postoperative mobilization and rapid rehabilitation.

External fixators are used in orthopaedic surgery to maintain the stumps at the ends of a fractured bone in position and allow the recalcification, consolidation and formation of a bone callus.

In general, the external fixators lock suitable bone screws or pins into position which, inserted inside each of the two stumps in which the bone was fractured, serve to maintain the ends firm and stable.

In this way, the external fixators help stabilize and immobilize a fractured bone to allow its reconstruction, facilitate the recalcification of any size fracture, or even accelerate the healing of significant chronic and/or traumatic wounds.

At the same time, the external fixators allow for the direct medical surveillance of the limbs, i.e. any superficial wounds, the neurovascular state or any muscle contractures in the treated limb, with obvious benefits for the patients.

Specifically, if the fractured bone is a bone that extends mainly in length such as the femur, tibia, fibula, radius, ulna or humerus, the fracture is locked with at least two bone screws for each stump, which are usually coplanar and parallel between them, they are aligned with a main direction of extension of the bone to be strengthened, which coincides with a prevalent extension direction of the fixator device and are placed on the same side of the fractured bone, perpendicular to the bone itself.

However, every fracture is different and therefore the treatment mode of each bone lesion can considerably vary depending on the size of the person, the dimensions of the fractured bones, and the type of lesion.

For example, it may be necessary to apply the bone screws in a converging configuration in order to insert them in the fractured bone in several, inclined parts.

For this reason the currently known external fixators have suitable support guides, shaped as straight or curved guides, configured to adapt to the size of the patient and to the extension of the fractured part and to support a plurality of locking elements of the respective bone screws.

The external fixators currently known in the art do not offer much flexibility in managing the intervention modalities on the fracture to be cured and are not always easy to apply or comfortable for the patient, because it is not always possible to position each bone screw as desired.

The bone screws are in fact applied to the bone to be strengthened when they are already inserted in the respective locking elements, serving, initially, for guiding the insertion of the bone screw in the bone and then, subsequently, locking the screws themselves into position.

It follows that within the operating surgery field, at the moment of insertion of the bone screws, all the remaining components of the external fixator are also present, such as the support guides and the locking elements, cluttering the operating field and making the application of the bone screws more complex, with a consequent increase in the duration of the surgery.

It is not always therefore possible to lock the bone screw in the desired direction. Furthermore, if the fracture is close to one end of the fractured bone, finding the optimum point of insertion of each bone screw is always complex, as one of the two bone stumps has reduced dimensions.

Other critical aspects of known external fixators are given from the mode with which each locking element is fixed to the support guides.

In fact, connecting bars are usually arranged between the support guides and each locking element can be fixed to a connecting bar or directly to a support guide.

For fixing, each locking element is usually integrated in a locking device which also comprises a coupling element configured to couple the locking element to the connecting bar and/or to the support guide.

In the locking device, the coupling element can be associated with the locking element or integrated within it. For example the coupling element can be realized by means of a body provided with a seat that is configured to receive the connecting bar on which a further seat for receiving a bone screw can also be present. Alternatively, the coupling element and the locking element can be interconnected by means of junction elements such as pins, screws and bolts.

The locking device therefore makes it possible to select in an appropriate manner, during a step of positioning the bone screw, the position and orientation of each bone screw with respect to the main direction of extension of the bone to be strengthened, that is, the arrangement of the locking element and the coupling element and therefore the configuration of the external fixator.

In order to reduce the duration of the surgery as much as possible, the locking device must ensure rapidity in the assembly of the locking element and coupling element in the external fixator, as well as fast locking of the position of the locking element and the coupling element with respect to the bone to be strengthened, when such a step of positioning the bone screw is finished, possibly without the use of external fixing devices.

The configuration of the external fixator, i.e. the configuration of each locking device of the bone screw, must remain unchanged in time for the entire period in which the external fixator is applied to the patient. To obtain this, the realization of the coupling element is critical, configured to couple the locking device to the connecting bar and/or to the support guide, which must ensure the stability and rigidity of the locking over time since the bone screw must remain locked over time in the same position and orientation established during surgery.

Also of particular interest is the possibility of varying the biomechanical performance of the external fixator during the healing process, so as to make it suitable for the actual bone calcification phase.

It is particularly important to check the amount of "force" applied to the bone callus with external fixators. The term "force" is intended as a mechanical stimulus applied to the callus of the fracture or to the newly-formed callus which assists the optimal reformation of the bone callus.

In fact, if force is applied too early or too late, there is a risk of applying an undesired compression to the fracture point with the consequent misalignment and/or shortening of the two parts of the fractured bone, or with the consequent undesired shortening of the limb previously subjected to elongation.

In an initial step of creating the callus, locking the two stumps of the fractured bone in position is usually recommended for preventing any movement between the two stumps themselves.

Then, and only when decided by the treating surgeon to allow a better vascularization of the callus and thus faster healing, it is advisable to allow small movements which, by avoiding excessive compression, act as a stimulus for the bone callus itself.

Object of the Invention

In this context, the technical task of the present invention is to provide a locking device for an external fixator for bone fractures which obviates the drawbacks in the prior art as described above.

In particular, an object of the present invention is to provide a locking device comprising a locking element of a bone screw and a coupling element configured to engage the locking device to the external fixator, which allows the easy orientation and positioning of the locking element during a positioning step and which ensures the stable and rigid fixing of the locking element in position, in a fixing step following the positioning step.

A further object of the present invention is to propose a locking device for an external fixator for bone fractures which makes it possible to manually orient and position the bone screw in the positioning step and manually lock the bone screw in position in the fixing step.

A different object of the present invention is to propose a locking device for an external fixator for bone fractures which is both simple and not costly to produce.

The stated technical task and specified objects are substantially achieved by a locking device for an external fixator for bone fractures, comprising the technical features disclosed in one or more of the appended claims.

BRIEF DESCRIPTION OF DRAWINGS

Additional features and advantages of the present invention will become more apparent from an approximate, and thus non-limiting, description of a preferred, but non-exclusive embodiment of an external fixator for bone fractures comprising a locking device, as illustrated in the appended drawings, in which.

DETAILED DESCRIPTION OF PREFERRED EMBODIMENTS OF THE INVENTION

Figure 1:
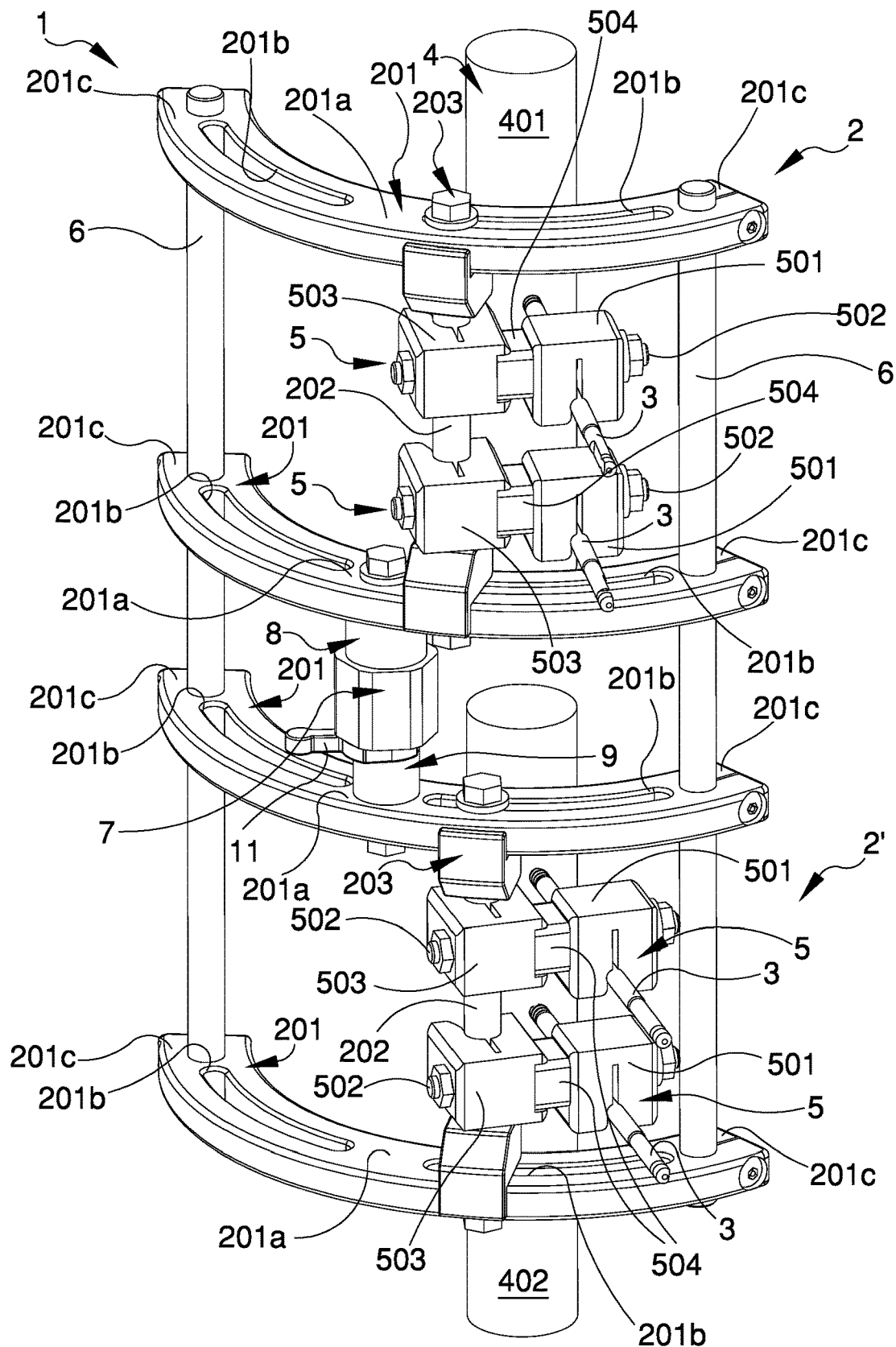
FIG. 1 is a perspective view of an external fixator for bone fractures according to the present invention comprising a pair of support units, each comprising a pair of curved supports, fixed together by a support pin, to which a pair of locking devices are fixed which support respective bone screws inserted in stumps of a fractured bone.

In accordance with the present invention, the number 1 is used herein to indicate an external fixator for bone fractures, as shown in FIGS. 1 to 13.

It should be noted that in the present description, the same elements are indicated in the various figures with the same numbers.

The external fixator 1 comprises at least two support units for removably supporting bone screws 3. For simplicity of representation, a support unit is indicated with number 2 while the other support unit is indicated with the number 2' even though there are no differences between the support units 2, 2'.

Figure 2:
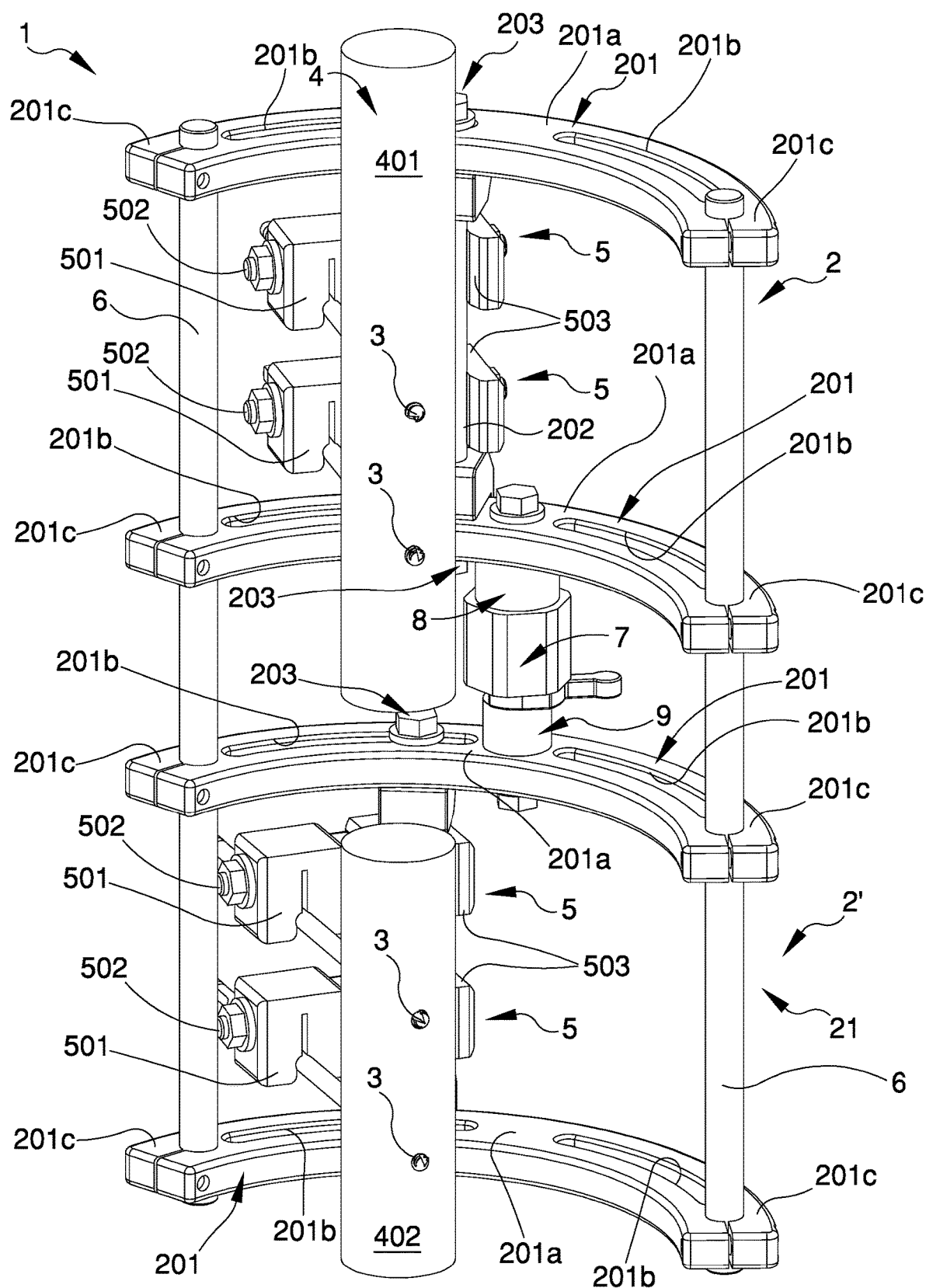
FIG. 2 is a further perspective view of the fixator of FIG. 1.

FIGS. 1 and 2 schematically show a bone 4 fractured into two stumps 401 and 402. A pair of bone screws 3 is inserted in the first stump 401, the other pair of bone screws 3 is inserted into the other stump 402.

Each support unit 2, 2' comprises a pair of support bodies 201, which are curved.

The external fixator can comprise a single support pin 202 or a pair of support pins 202, each of which can be fixed to one or both of the support bodies 201, as will be explained in more detail below.

Figure 6:
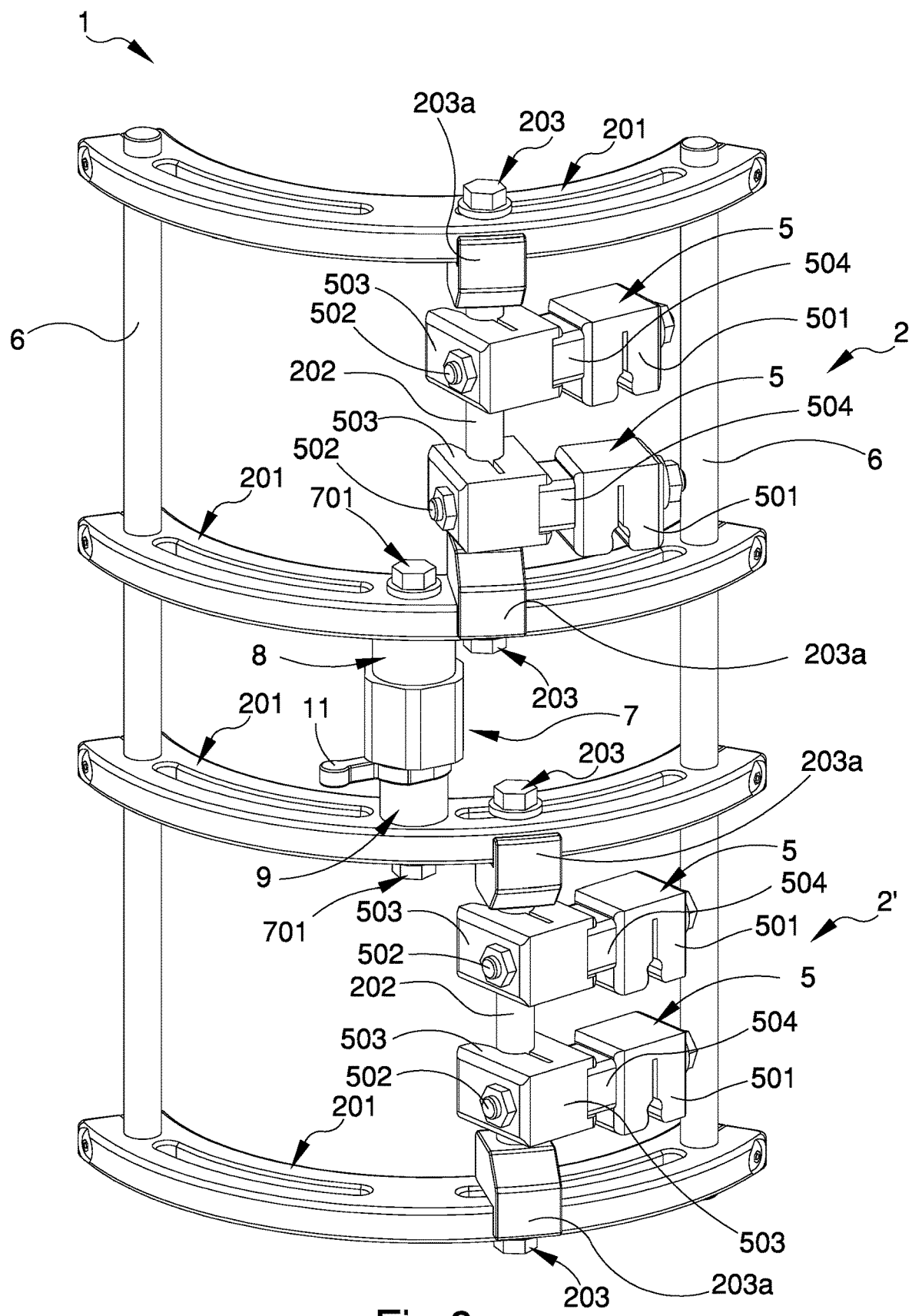
FIG. 6 shows a perspective view of the external fixator of FIG. 1 in a non-operating configuration in which the bone screws are not present and one of the locking devices is arranged, from an angular point of view, in a different way with respect to the external fixator of FIGS. 1 and 2.
Figure 7:
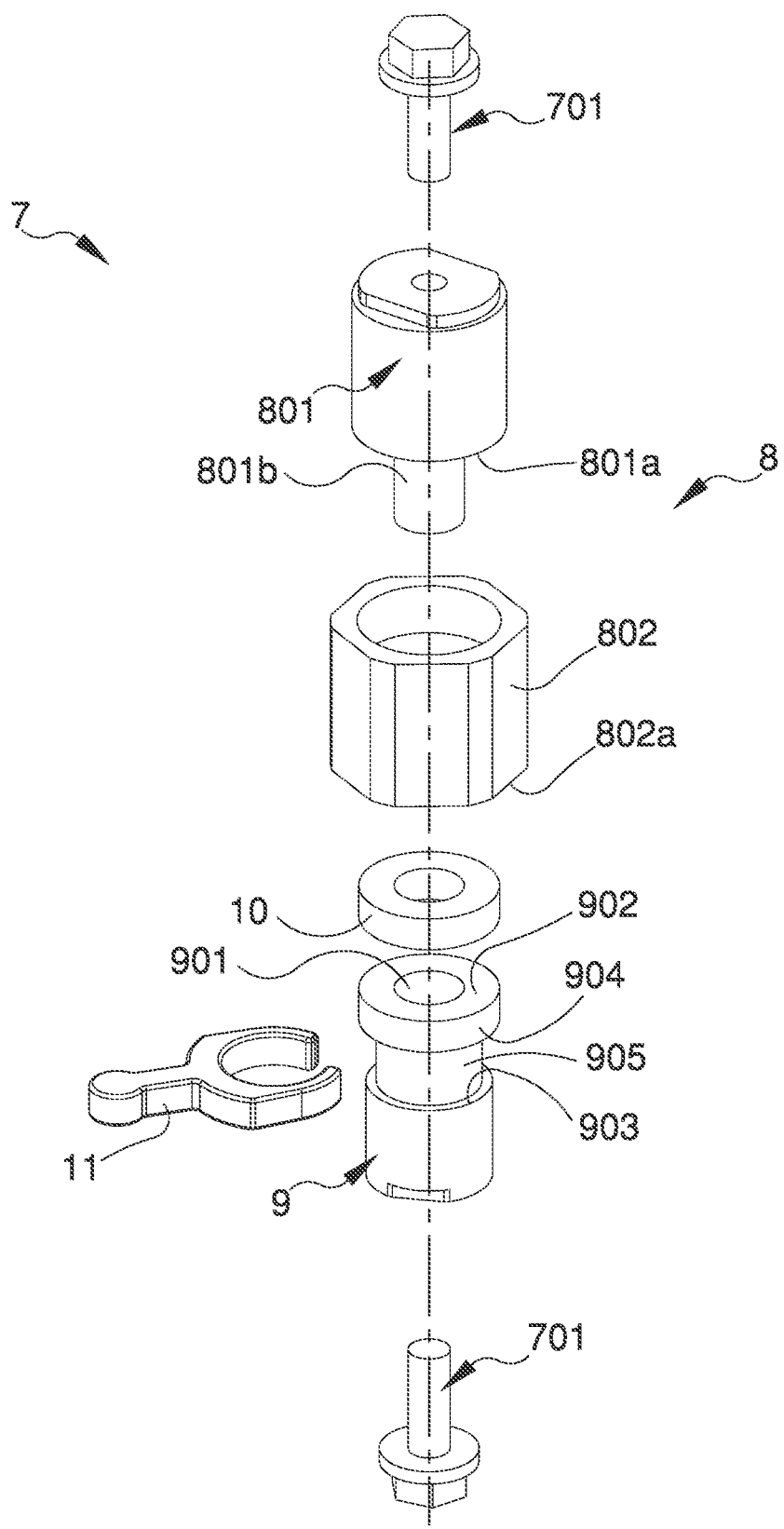
FIG. 7 shows an exploded perspective view of the variation device of the external fixator of FIGS. 1, 2 and 6.
Figure 8:
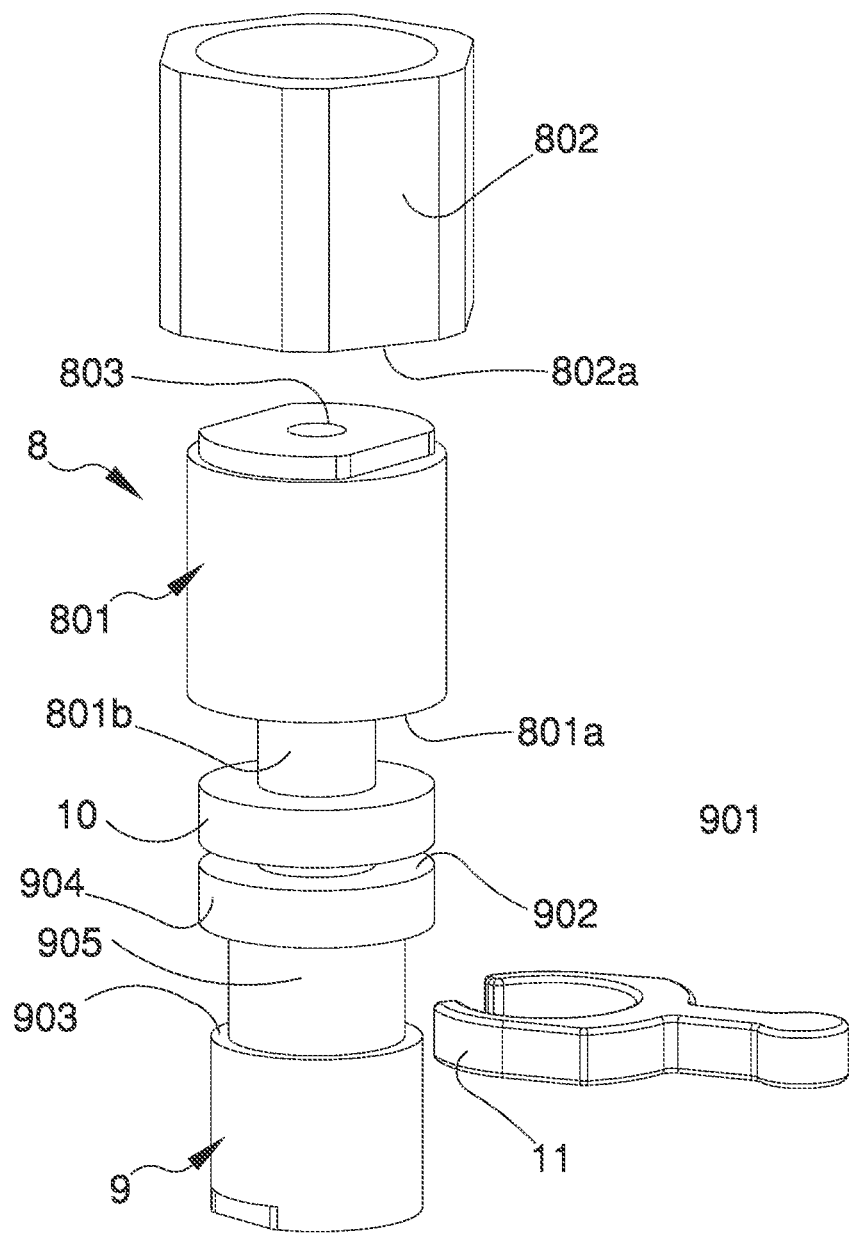
FIG. 8 shows the variation device of FIG. 7, partly assembled, wherein some parts have been removed for clarity.

It should be noted that the external fixator 1 shown in FIGS. 1, 2 and 6 comprises, in each support unit 2, 2' a single support pin 202, which is fixed to both support bodies 201 of the support unit.

Figure 11:
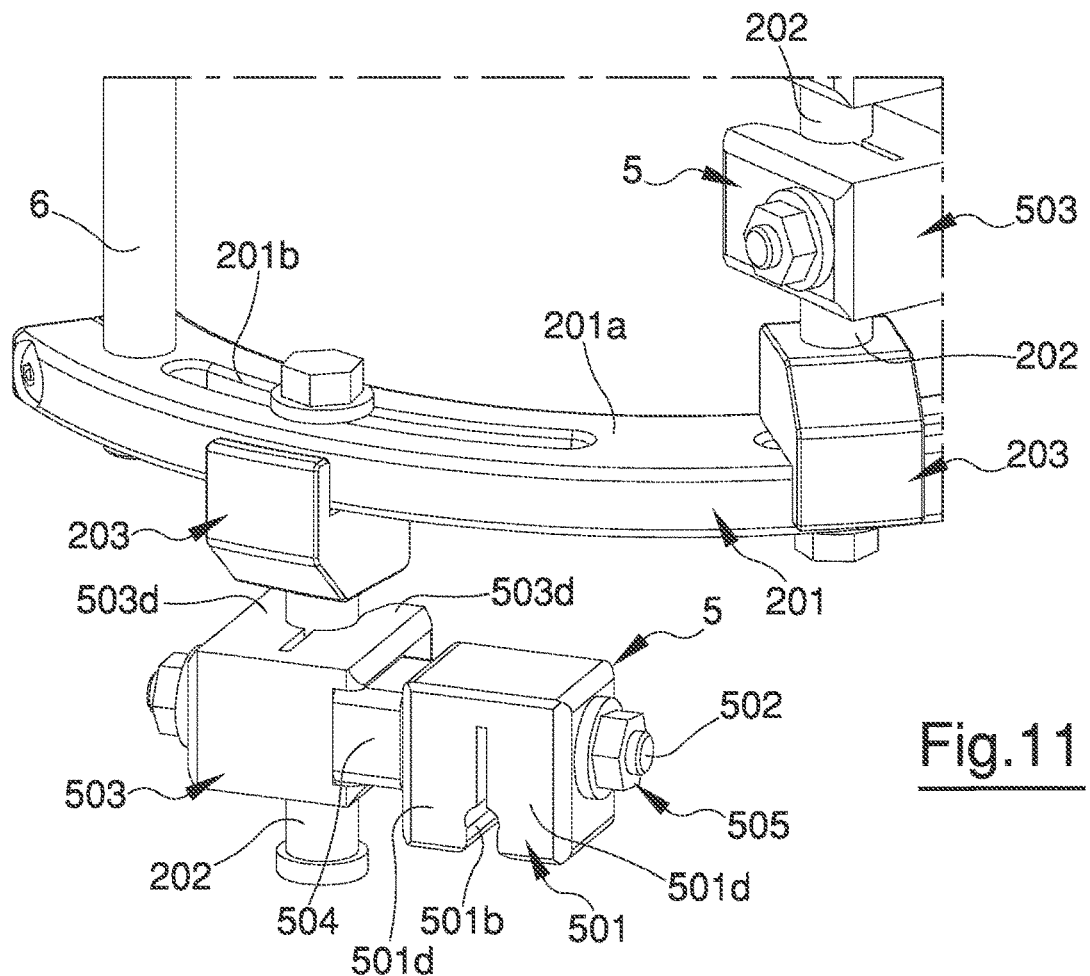
FIG. 11 shows a detail of a variant of the external fixator of FIG. 6, wherein a support pin has an end fixed to only one of the support bodies, the other end being free.

Alternatively, as shown in FIG. 11, the support unit 2' of the external fixator 1 can comprise a support pin 202 which is fixed to both the support bodies 201 and a further support pin 202' which is fixed to a single support body 201 and extends externally with respect to the support unit 2'.

Preferably, each support pin 202 is made of carbon fibre, which ensures rigidity and lightness.

The support bodies 201 are curved in order to be able to at least partially surround a limb, such as a leg or an arm, containing the fractured bone.

It should be noted that the support bodies 201 extend over an arc of circumference and that this arc of circumference extends for three/eighths (⅜) of the entire circumference. It has been experimentally noted that such an angular extension of the support bodies 201 is particularly advantageous in the case of fractures of long bones of the arm or leg to adequately envelop the limb without overly hindering movements.

Preferably, the support bodies 201 are mutually identical and have a shape specifically designed for the limb for which they are intended to be associated.

However, according to an alternative embodiment of the external fixator of the present invention, not shown, each support body 201 has its own shape that is different from the shape of the other support bodies 201, to better adapt to patients' application needs.

Each support unit 2 or 2' further comprises a pair of locking devices 5 of a bone screw, each of which comprises a respective locking element 501 for removably locking a bone screw 3.

It should be noted that if necessary, a support unit 2 or 2' can also comprise more than two locking devices 5, if one of the bone stumps requires the insertion of more than two bone screws.

In detail of the present invention, each locking device 5 comprises a locking pin 502, which is configured to support the locking element 501. The locking element 501 can rotate around the locking pin 502 and in addition, each locking device 5 is configured to rotate around the support pin 202 and to slide along the support pin 202 in such a way as to allow a versatile positioning of each bone screw 3, in a positioning step of the bone screw.

Thanks to the fact that the locking device 5 can rotate and slide with respect to the support pin 202 and that the locking element 501 can rotate around the locking pin 502 in the locking device 5, the positioning of each locking element 501, and hence of each bone screw 3, with respect to the fractured bone 4, can be easily modified according to needs.

The inclination of the bone screws 3 with respect to the bone 4 can be selected in the most appropriate manner, as each locking element 501 can be positioned in different operating conditions. In addition, in each support unit 2 or 2', a locking device 5 has a position that is independent of the position of the other locking device 5 and therefore the two bone screws 3 of each support unit 2 or 2' can have a different inclination with respect to the fractured bone 4 and thus ensure greater freedom of insertion in the fractured bone 4 itself. For example, note that in FIG. 6, one of the locking devices 5 of the support unit 2 is inclined differently than the other locking device 5.

Figure 3:
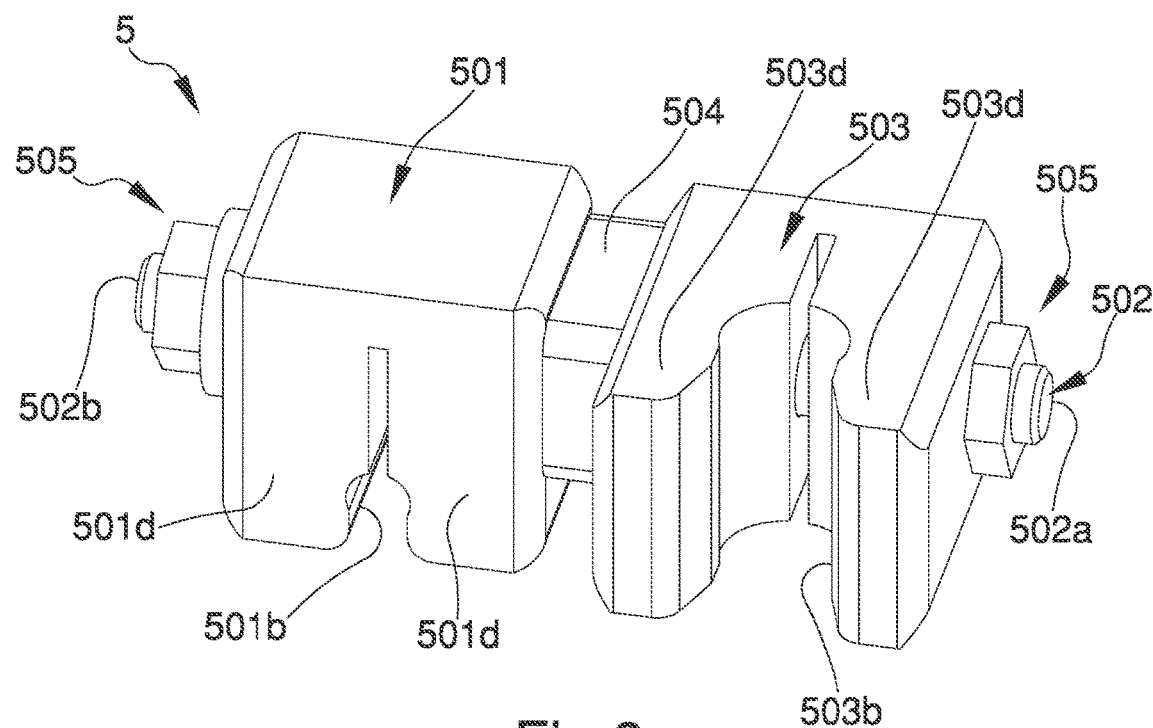
FIG. 3 is a perspective view of a locking device according to the present invention comprising a locking element of a bone screw and a coupling element in order to allow the coupling to the support pin.
Figure 4:
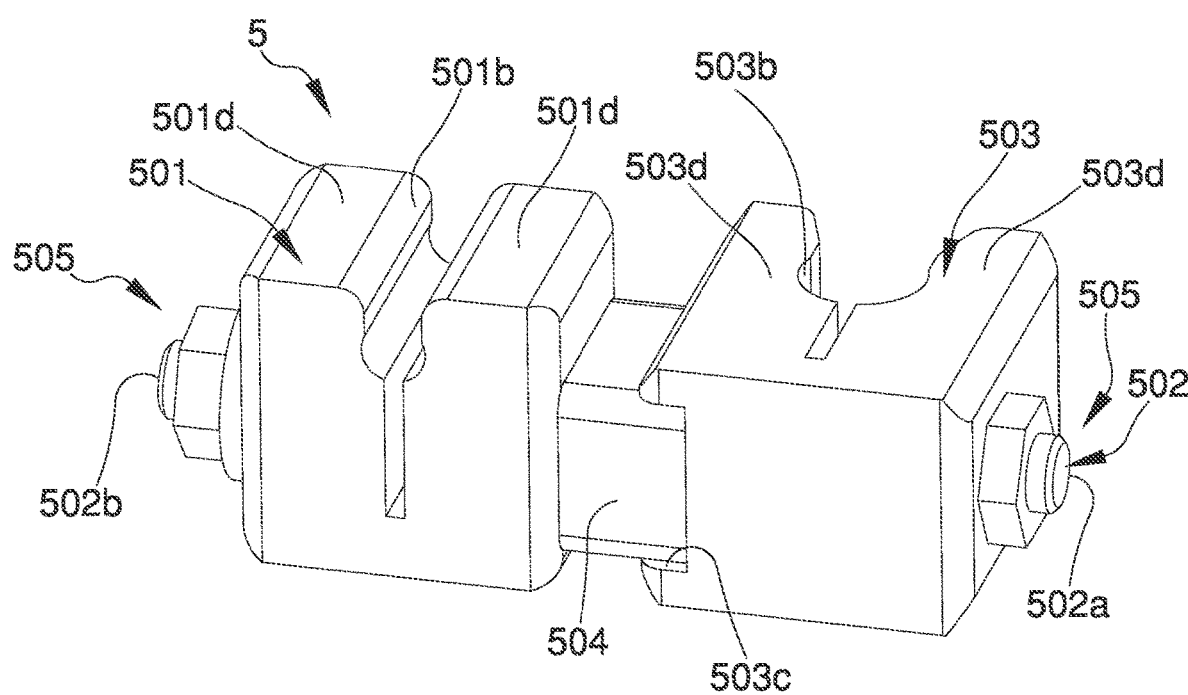
FIG. 4 is a further perspective view of the locking device of FIG. 3.
Figure 5:
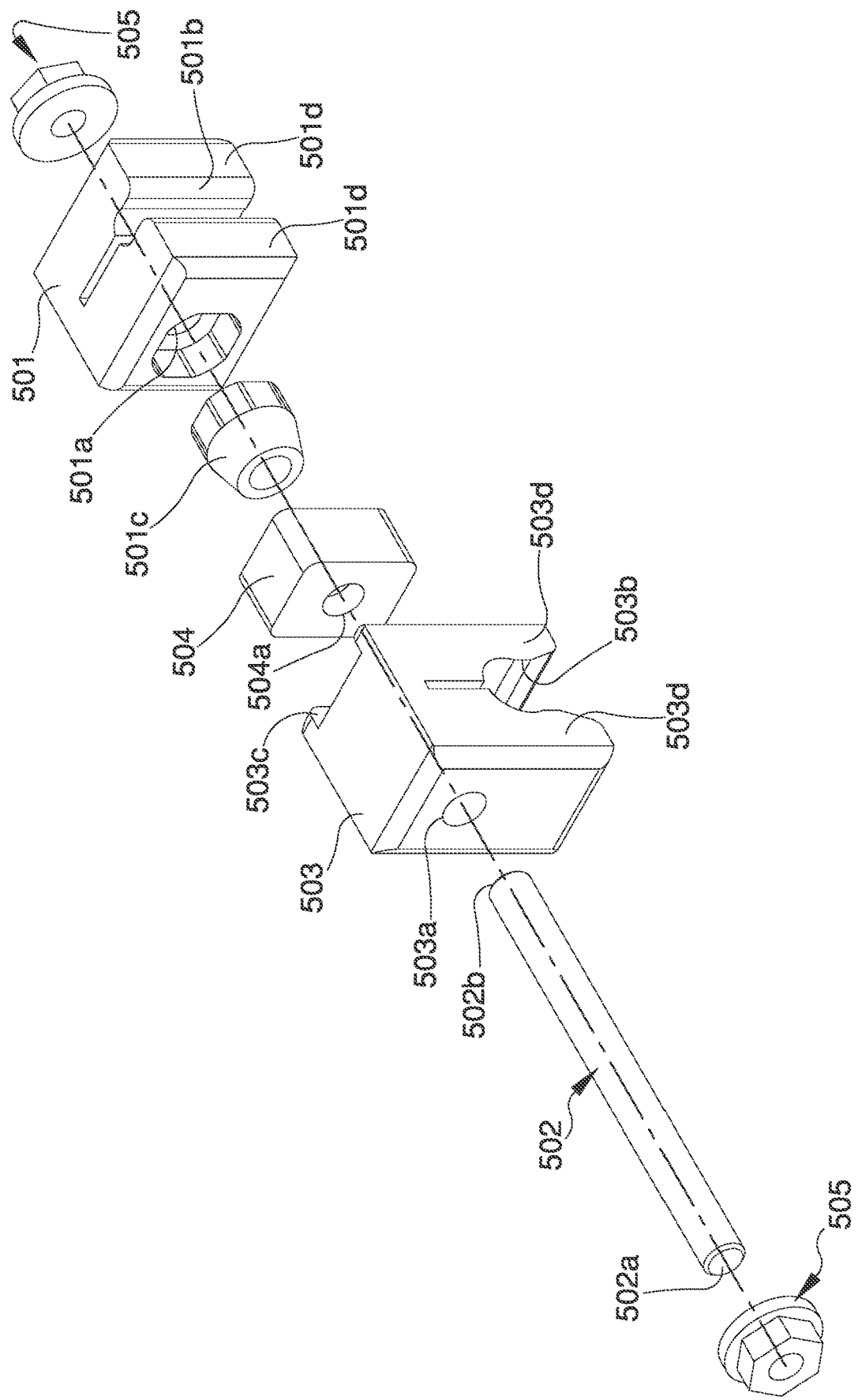
FIG. 5 shows an exploded view of the locking device of FIGS. 3 and 4.

As shown in FIGS. 3 to 5, each locking element 501 is shaped like a gripper clamp provided with a through opening 501a in order to be inserted in the respective locking pin 502. The locking element 501 further comprises a locking seat 501b which allows the housing of the bone screw 3, in particular of a head end of a bone screw 3.

It should be noted that the locking element 501 is provided with a pair of opposite jaws 501d, between which the respective locking seat 501b is defined. On the opposite side with respect to the jaws 501d, there is a hinge line (not shown) that joins the jaws 501d, allowing the locking element 501 to bend to lock the bone screw.

The through opening 501a of the locking element 501 is arranged transversely with respect to a prevailing extension of the jaws 501d.

Each locking device 5 comprises, in addition, a coupling element 503 which is provided with a coupling seat 503b configured to receive the support pin 202 by snap-fit coupling.

The coupling element 503 is configured to allow, during the positioning step of the bone screw 3, a rotation of the locking device 5 around the support pin 202 and a sliding of the locking device 5 along the support pin 202.

Thanks to the presence of the locking seat 501b of the locking element 501, configured to receive the head end of the bone screw 3, and thanks to the presence of the coupling seat 503b of the coupling element 503, easily engageable on the support pin 202, the locking device 5 can easily lock the bone screw 3 and be easily locked to the support pin 202, after the insertion of the bone screw 3 in a bone stump 401, 402.

In other words, the bone screw 3 is adjustable and fixable on the bone 4 according to the needs of the patient and can be attached and locked to the locking device 5 after this insertion. This allows each locking device 5 to be coupled to a support pin 202 independently from the remaining locking devices 5, each support body 201 and each support unit 2, 2'.

It follows that the bone screws 3 can be inserted in the bone 4 only in the presence of the locking device 5 but not of the entire external fixator 1, and this gives the physician great freedom in positioning the bone screw 3 itself.

The coupling element 503 is shaped like a gripper clamp and is provided with a through opening 503a in order to be inserted in the respective locking pin 502. The coupling element 503 is provided with a pair of opposite jaws 503d, between which the respective coupling seat 503b is defined. On the opposite side with respect to the jaws 503d, there is a hinge line (not shown) that joins the jaws 503d, allowing the coupling element 503 to bend to couple with the support pin 202.

The through opening 503a is arranged transversely with respect to a prevailing extension of the jaws 503d.

According to the present invention, the locking device 5 comprises a fixing element, which is configured to allow the rotation of the locking element 501 with respect to the locking pin 502, the rotation of the locking device 501 around the support pin 202 and the sliding of the locking device 501 along the support pin 202 during the step of positioning the bone screw 3. The fixing element is further configured to allow a user to manually fix a position of the locking element 501 into the locking device 5 and the locking device 5 with respect to the support pin 202 in a fixing step, which is subsequent to the positioning step, to lock a configuration of the locking device 5 in the external fixator 1.

Thanks to the fixing element, the locking device 5 can advantageously be positioned, or locked, in the external fixator 1 with the consequent simplicity of use of the locking device 5 itself.

The fixing element comprises a stabilizing element 504, which is provided with a respective through opening 504a to be inserted into the locking pin 502 between the coupling element 503 and the locking element 501 so that, in the fixing step, as soon as the stabilizing element 504 simultaneously abuts both the locking element 501 and the coupling element 503, a possible rotation of the locking element 501 is locked with respect to the locking pin 502.

The stabilizing element 504 is externally shaped at least on one side so as to be housed at least partially in a respective recess 503c of the coupling element 503, and on the other side is internally shaped to at least partly abut the locking element 501, for example with a conical coupling 501c housed at least partially in the locking element 501 itself.

The stabilizing element 504 and the respective recess 503*c* of the coupling element 503, in which the stabilizing element 504 is housed, are of conjugate shape and form a prismatic coupling.

In this way, when the bone screw 3 is locked in position in the respective locking element 501, the conical coupling 501*c*, as well as the external shape of the stabilizing element 504, allows the stabilizing element 504 to angularly lock the locking element 501 with respect to the locking pin 502.

The stabilizing element 504 is an anti-rotation element.

Figure 12:
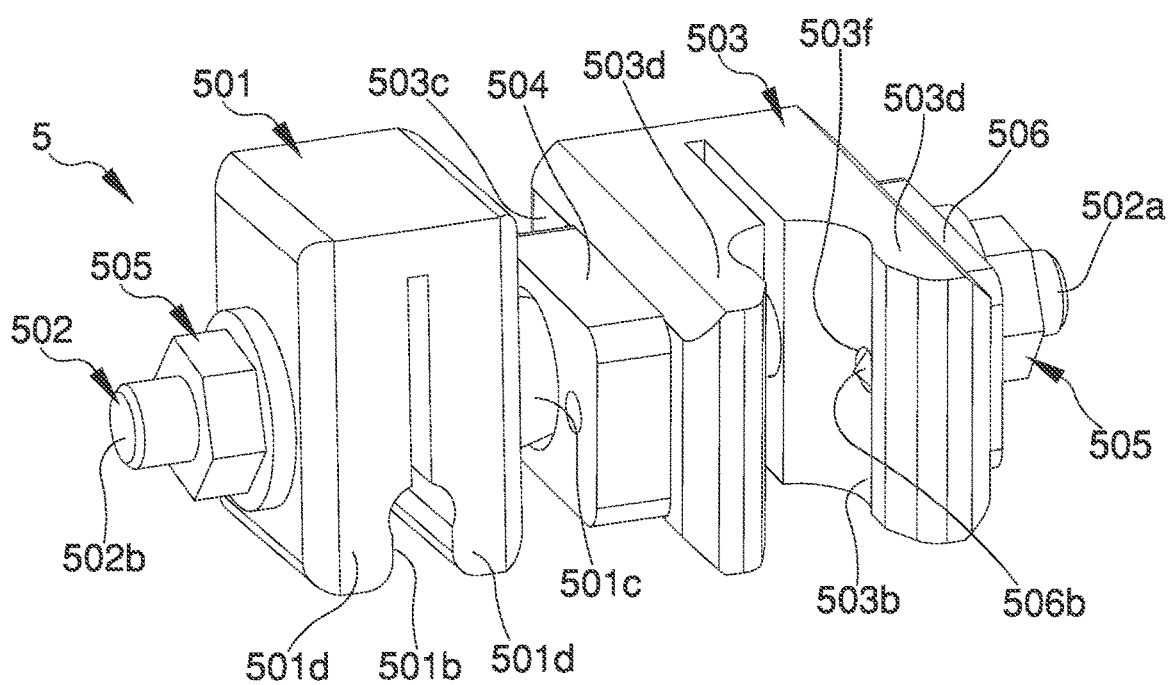
FIG. 12 shows a variant of the locking device of FIGS. 3 to 5, which comprises a stabilizing device and a further stabilizing device of the configuration of the locking device.
Figure 13:
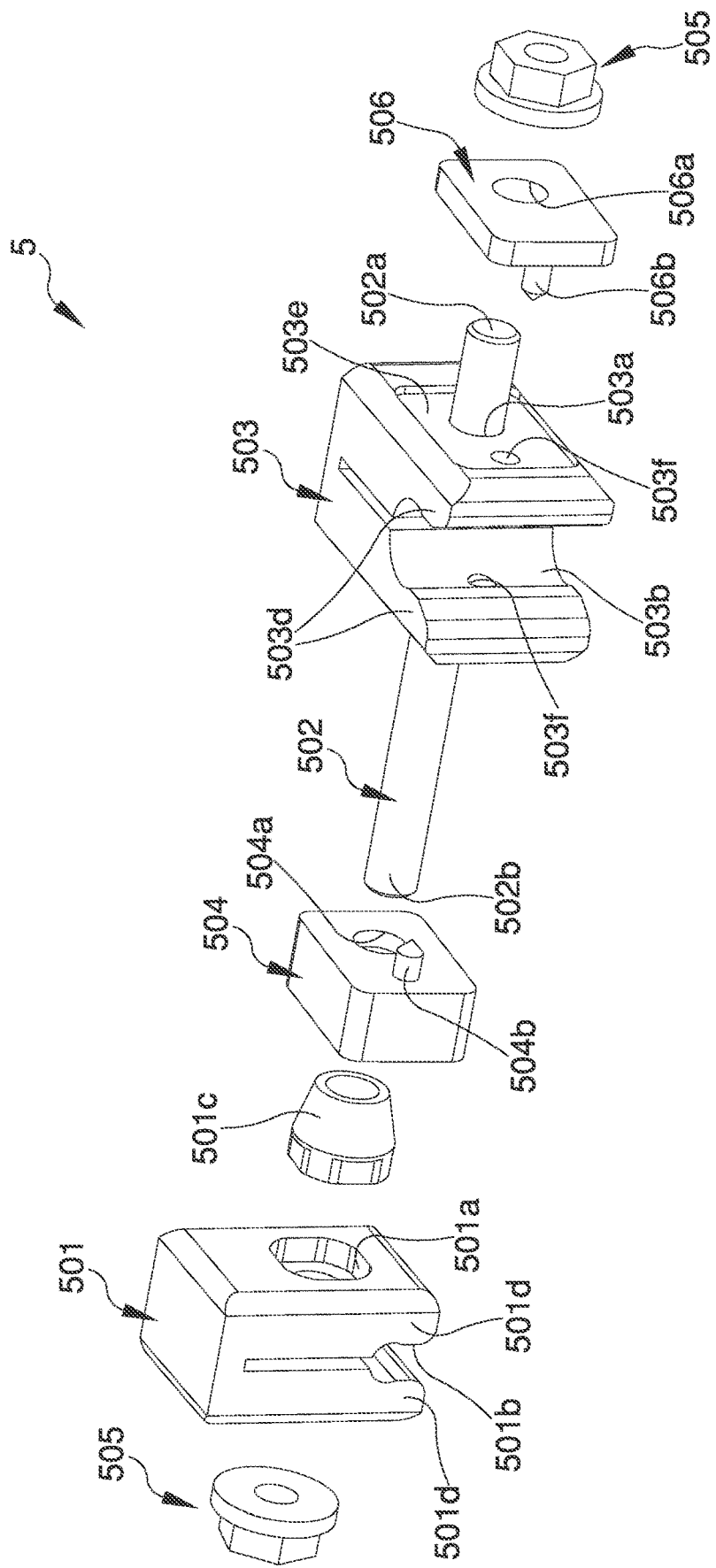
FIG. 13 shows an exploded view of the locking device of FIG. 12.

According to a variant shown in FIGS. 11 to 13, the fixing element also comprises a further stabilizing element 506 which is provided with a respective through opening 506*a* configured to receive the locking pin 502. The coupling element 503 is arranged between the stabilizing element 504 and the further stabilizing element 506 so that, in the fixing step, the coupling element 506 abutting simultaneously both the stabilizing element 504 and the further stabilizing element 506, the rotation of the locking device 5 around the support pin 202 and the sliding of the locking device 5 along the support pin 202 are locked.

The further stabilizing element 506 is externally shaped at least on one side so as to be housed at least partly in a further recess 503*e* of the coupling element 503, which is arranged on the opposite side with respect to the recess 503*c*.

The further stabilizing element 506 and the respective further recess 503*c* in which the further stabilizing element 506 is housed are of conjugate shape and form a prismatic coupling.

The further stabilizing element 506 cooperates with the stabilizing element 503 to angularly lock the coupling element 503 with respect to the locking pin 502 and with respect to the support pin 202 and perform the function of making the configuration of the locking device 5 stable with respect to the support pin 202 itself.

The further stabilizing element 506 is also an anti-rotation element.

The jaws 503*d* of the coupling element 503 have respective through openings 503*f*, configured to receive a coupling pin 504*b* of the stabilizing element 504 and a further coupling pin 506*b* of the further stabilizing element 506, which are arranged to be coupled with the support pin 202 when the locking device 5 is in the fixing step and the coupling element 503 is coupled to the support pin 202.

Preferably, the coupling pin 504*b* and the further coupling pin 506*b* have pointed ends.

The stabilizing element 504 and the further stabilizing element 506 are made of steel and therefore when the coupling pin 504*b* and the further coupling pin 506*b* are coupled with the support pin 202, the pointed ends of the coupling pin 504*b* and of the additional coupling pin 506*b* create respective indentations in the support pin 202 which provide a stable coupling of the locking device 5 to the support pin 202 and prevent its rotation.

The coupling pin 504*b* and the further coupling pin 506*b* extend for a length such as to interfere with the support pin 202 in the step of fixing the locking device 5.

Thanks to the coupling pin 504*b* of the stabilizing element 504 and further coupling pin 506*b* of the further stabilizing element 506, configured to be received in the through openings 503*f* of the jaws 503*d* and couple by engaging with the support pin 202 and creating indentations in the same, the stability of the coupling of the coupling element 503 with the support pin 202 is even more guaranteed because it even further locks the rotation of the locking device 5 around the support pin 202 and the sliding of the locking device along the support pin 202.

The fixing element comprises a pair of clamping elements 505. Each locking pin 502 comprises, in fact, respective terminal ends 502*a*, 502*b*, each of which is configured to receive a respective clamping element 505 such as to fix the angular position of the locking element 501 with respect to the locking pin 502 and the coupling element 503 with respect to the support pin 202. In doing so, the locking element 501 is locked in an angular position with respect to the locking pin 502, and the locking device 5 with respect to the support pin 202.

The clamping elements 505 are configured to abut the locking element 501 on one side and the coupling element 503 on the other side so as to clamp the locking element 501, the coupling element 503 and the stabilizing element 504 to each other.

In the case wherein the fixing element also comprises the further stabilizing element 506, the clamping elements 505 are configured to abut the locking element 501 on one side and the further stabilizing element 506 on the other, so as to clamp the locking element 501, the stabilizing element 504, the coupling element 503 and the further stabilizing element 506 to each other.

A threaded coupling is present between the terminal ends 502*a*, 502*b* of the locking pin 502 and the clamping elements 505, for example a screw/bolt as shown in the accompanying figures. Advantageously, while being very simple to manufacture and inexpensive, this type of coupling is also simple to use during surgery. The tightening of the locking device 5 is therefore very quick, and considering the snap-fit coupling of the coupling element 503 to the support pin 202, this allows the rapid application of the locking device 5 to the support pin 202 and thus the rapid configuration of the external fixator 1 and consequently the rapid application to the patient.

When the locking device 5 is clamped and is angularly locked with respect to the support pin 202, the inner coupling between the locking element 501 and the coupling element 503 by means of the stabilizing element 504 and the further stabilizing element 506 cooperates with the clamping elements 505 to maintain the locking element 501 in position without further possible rotations.

It should be noted that the support pin 202, or the pair of support pins 202, can be fixed to the support bodies 201 in an adjustable position.

Each support body 201 comprises, in fact, a central portion 201*a* and a pair of slots 201*b* that extend along the support body 201 starting from the central portion 201*a*.

Each support pin 202 is provided with opposite terminal ends which, if the support pin 202 is fixed to both the support bodies, are both fixed in the slots 201*b*, arranged facing each other in the respective support bodies 201.

Alternatively, as shown in FIG. 11, if the support pin 202 is fixed to a single support body 201, one of the terminal ends of the support pin 202 is free, while the other is fixed to one of the support bodies 201.

Also in this case, advantageously, the terminal ends are fixed in the slots 201*b* by means of fixing elements 203 which, for simplicity of construction and use, form a threaded coupling, for example screw/bolt, which also includes a support bracket 203*a*.

The external fixator 1 comprises, in addition, a pair of connecting bars 6 to connect the two support units 2, 2' together.

It should be noted, as hereinafter explained with greater detail, that in the pair of support bodies 201 of each support unit 2 or 2', joined by connecting bars 6, a peripheral support body 201 and a central support body 201 can be identified.

The central support body 201 of a support unit 2 is facing another central support body 201 of the other support unit 2'.

If, as shown in FIG. 11, the support pin 202 is fixed to a peripheral support body 201, the locking device 5 extends externally with respect to the support unit 2' and therefore the size of the external fixator 1 can be longitudinally extended, in the case of fractures that require this configuration of the external fixator 1.

The support bodies 201 of each support unit 2 or 2' have edge ends 201c equipped with through openings for receiving the connecting bars 6. In detail, the connecting bars 6 are inserted in the support bodies 201 longitudinally and are fixed to the support bodies with screws.

Thanks to the connecting bars 6, the support units 2, 2' are made mutually integral in order to realize a structure connected in a single body. However it should be underlined that the external fixator 1 is not a rigid structure, but has an elasticity which is determined by the type of material selected for the support bodies 201, the support pin 202 and the locking pin 502 of each support unit 2 or 2' and for the connecting bars 6.

For example, if the selected material is a light aluminium alloy which has intrinsic elastic properties, the two support units 2 or 2' can bend and allow limited micro-movements, necessary in a phase of bone callus formation.

In use, the physician inserts the bone screws 3 in the stumps 401, 402 of the fractured bone. Subsequently, for each bone screw 3 already inserted, the physician correctly positions each locking device 5 with respect to the support pin 202. In detail, the physician initially adjusts the position of the locking element 501 with respect to the locking pin 502 in such a way that the coupling seat 501b can receive the head end of the bone screw 3 and then inserts the support pin 202 in the coupling seat 503b of the coupling element 503.

By acting on the clamping elements 505, the physician can quickly and simply lock the locking devices 5 in position on the support pin 202 and assemble the locking device 5 in position.

Assembling the various locking devices 5 in position, the configuration of the external fixator 1 can be rapidly assembled.

We wrote that the external fixator 1 comprises two support units 2, 2' for removably supporting the bone screws 3, wherein each support unit 2 or 2' comprises a pair of support bodies 201 which are curved, and only one support pin 202, or a pair of support pins 202, to which a pair of locking devices 5 are fixed, in the same support pin 202 or in the respective support pins 202, each of which supports a respective locking element 501 to allow a versatile positioning of each bone screw 3.

According to one aspect of the present invention, the external fixator 1 also comprises a variation device 7 fixed on one side to a support unit 2 and the other side to the other support unit 2', wherein the variation device 7 is configured to allow or lock a controlled variation of the distance between the support units 2, 2' themselves.

As shown in detail in FIGS. 7 to 10, the variation device 7 comprises a first part 8 fixed to the support unit 2, a second part 9 fixed to the other support unit 2', and a deformable element 10 interposed between the first part 8 and the second part 9 to allow said controlled variation.

Thanks to the variation device 7, when the physician deems it possible, the external fixator 1 can be allowed to have controlled movements in the bone area of the bone callus formation for a limited stroke, offering wider possible micro-movements thanks only to the elastic properties of the material with which the external fixator 1 is made.

In fact, while the external fixator 1 is still a structure with two support units 2, 2' integrally connected together, the variation device 7 interposed between the support units 2, 2' cooperates with the elasticity of the external fixator 1 to allow the two stumps 401, 402 to move farther from or closer to a maximum predetermined distance in such a way as to stimulate the formation of the bone callus.

The first part 8 comprises an inner body 801 and an outer body 802, which is fixed to the inner body 801 and externally surrounds the inner body 801, the deformable element 10 being interposed between the inner body 801 and the second part 9.

The inner body 801 is in fact provided with an abutment wall 801a and a tubular protrusion 801b extending from the abutment wall 801a.

The outer body 802 extends up to an edge 802a, which is free and an end edge.

The second part 9 comprises a compartment 901 which is shaped for slidably receiving the tubular protrusion 801b and is surrounded at the front by a rest wall 902.

The deformable element 10 is shaped like a ring and surrounds the tubular protrusion 801b so as to be interposed between the abutment wall 801a and the rest wall 902.

The deformable element 10 is made, for example, of silicone material.

Thanks to the shape of the first part 8 and the second part 9, the variation device 7 of the distance between the support units 2, 2' is made in a very simple and low-cost way with the deformable element 10 interposed between the first part 8 and the second part 9, whose compression causes the variation of the distance between the support unit 2 and the other support unit 2'.

The second part 9 comprises a stop wall 903, which is configured to receive in abutment a stop ring 11, shaped like an open ring 11a provided with a handle, that, when positioned on the stop wall 903, abuts the edge 802a of the outer body 802 by locking the controlled variation of the first part 8 with respect to the second part 9.

It should be noted that the second part 9 comprises a head area 904, which is delimited frontally by the rest wall 902 and is of greater diameter than an intermediate tubular area 905. The stop wall 903 delimits the intermediate area 905 on the part opposite the head area 904.

If we now consider the support bodies 201 of the external fixator, it can be noted that the first part 8 of the variation device 7 is fixed to one of the central support bodies 201 while the second part 9 of the variation device 7 is fixed to the other central support body 201.

Figure 9:
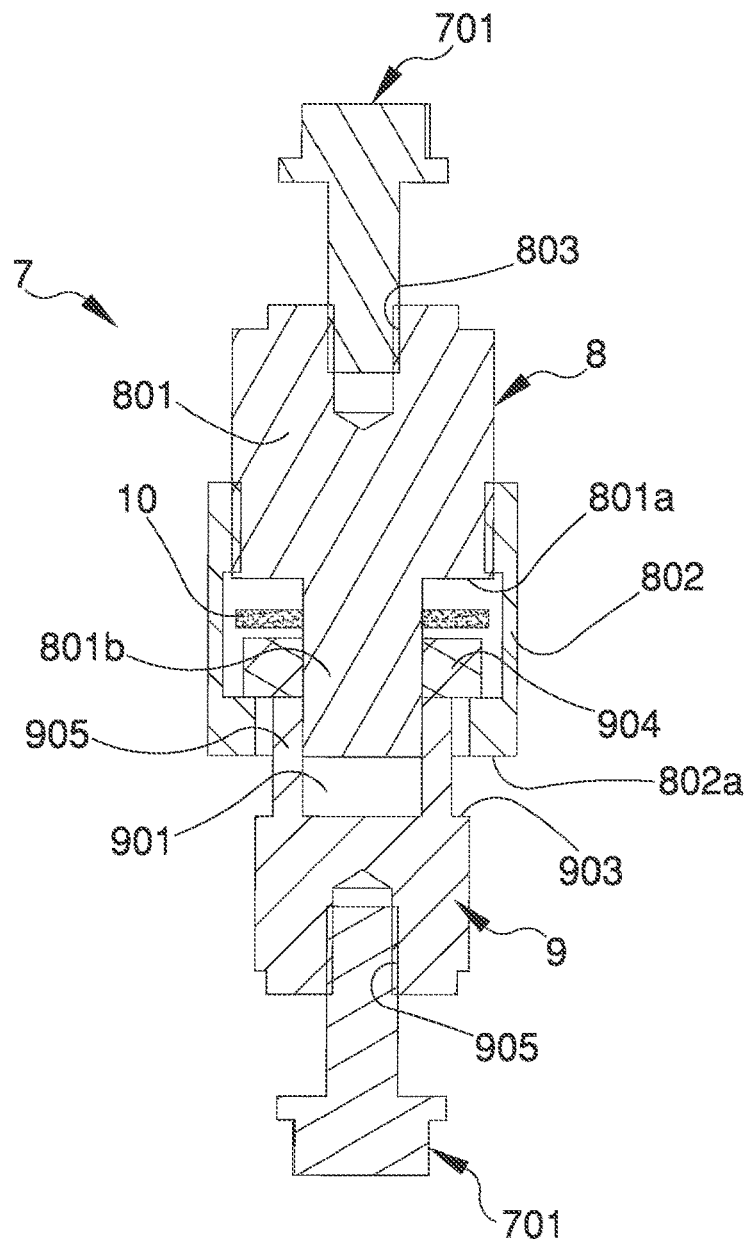
FIG. 9 shows a section view of the variation device of FIGS. 7 and 8, along the plane of section IX-IX of FIG. 10.
Figure 10:
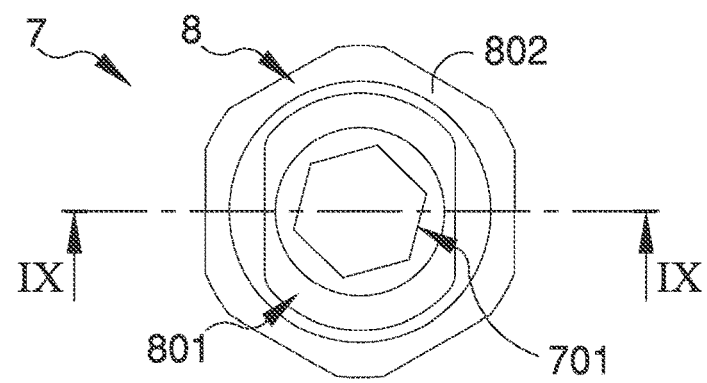
FIG. 10 shows a view from above of the variation device of FIGS. 7 and 8.

Coupling elements 701 are provided, for example a screw/nut screw coupling, to fix the first part 8 to a support body 201 and the second part 9 to another support body 201. For this purpose, as shown in FIG. 9, the first part 8 and the second part 9 have respective coupling seats 803 and 905, for receiving the coupling elements 701. Specifically, the seat 803 is arranged in the inner body 801.

In use, the external fixator 1 is initially positioned on the patient with the stop ring 11 in abutment against the stop wall 903 so as to lock the sliding of the inner body 801 of the first part 8 in the compartment 901 of the second part 9, from the moment that the stop ring 11 abuts the free edge 802a of the first part. The external fixator 1 can only make micro-movements due to the elasticity of the material with which the fixator is made.

Subsequently, when the physician removes the stop ring 11, the inner body 801 can slide in the compartment 901 and the deformable element 10 can be deformed by compression, crushed between the abutment wall 801a and the rest wall 902. Controlled movements are therefore possible in the bone area of the bone callus formation, since the external fixator 1 has elastic properties that allow the support unit 2 to vary its distance with respect to the other support unit 2' even while the external fixator 1, when the components have all been fixed between them, is a single body.

Advantageously, therefore, the constructional simplicity of the external fixator 1, integrating locking devices 5 and the variation device 7 according to the present invention, allows low-cost production but above all ease of application and use by a physician.

The invention claimed is:

1. A locking device (5) of a bone screw (3) for an external fixator (1) for bone fractures, the external fixator (1) comprising at least one support pin (202), wherein the locking device (5) comprises:
    a locking element (501) of the bone screw (3);
    a locking pin (502), which is configured to support the locking element (501), the locking element (501) being configured to rotate around the locking pin (502) in a positioning step of the bone screw;
    a coupling element (503), which is provided with a respective coupling seat (503b) configured to receive the support pin (202) by snap-fit coupling and to allow, during the bone screw (3) positioning step, a rotation of the locking device (5) around the support pin (202) and a sliding of the locking device (5) along the support pin (202); wherein the locking device (5) comprises:
    a fixing element (504, 505, 506), which is configured to allow the rotation of the locking element (501) with respect to the locking pin (502), and sliding of the locking device (5) along the support pin (202) during the positioning step and the fixing element is further configured to allow the manual fixing of a position of the locking element (501) in the locking device (5) and the locking device (5) with respect to the support pin (202) in a fixing step, which follows said positioning step, to lock a configuration of the locking device (5) in the external fixator (1);
    wherein the fixing element (504, 505, 506) comprises a stabilizing element (504), which is provided with a respective through opening (504a) configured to receive the locking pin (502), the stabilizing element (504) being arranged between the coupling element (503) and the locking element (501) so that, in the fixing step, with the stabilizing element (504) simultaneously abutting both the locking element (501) and the coupling element (503), a possible rotation of the locking element (501) with respect to the locking pin (502) is locked;
    wherein the fixing element (504, 505, 506) also comprises a further stabilizing element (506) which is provided with a respective through opening (506a) configured to receive the locking pin (502), the coupling element (503) being arranged between the stabilizing element (504) and the further stabilizing element (506) so that, in the fixing step, the coupling element (503) simultaneously abutting the stabilizing element (504) and the further stabilizing element (506), the rotation of the locking device around the support pin (202) and the sliding of the locking device along the support pin (202) are locked; wherein
    the coupling element (503) is shaped like a gripper clamp, and is provided with a pair of respective opposite jaws (503d) defining the coupling seat (503b), and it is provided with a through opening (503a), configured to receive the locking pin (502), which is arranged transversely with respect to a prevailing extension of said jaws (503d);
    wherein the jaws (503d) of the coupling element (503) have respective through openings (503f), configured to respectively receive a coupling pin (504b) of the stabilizing element (504) and a further coupling pin (506b) of the further stabilizing element (506), which are arranged to be coupled with the support pin (202) in the fixing step, such to further lock the rotation of the locking device (5) around the support pin (202) and the sliding of the locking device (5) along the support pin (202).

2. The locking device according to claim 1, wherein the stabilizing element (504) is externally shaped at least on one side so as to be housed at least partially in a recess (503c) of the coupling element (503) and is internally shaped on the other side to at least partly abut the locking element (501).

3. The locking device according to claim 2, wherein the stabilizing element (504) and the recess (503c) of the coupling element (503) are of conjugate shape.

4. The locking device according to claim 3, wherein the further stabilizing element (506) is externally shaped at least on one side so as to be housed at least partly in a further recess (503e) of the coupling element (503), which is arranged on the opposite side with respect to the recess (503c).

5. The locking device according to claim 4, wherein the further stabilizing element (506) and the respective further recess (503e) in which the further stabilizing element (506) is housed are of conjugate shape.

6. The locking device according to claim 1, wherein the locking element (501) is shaped like a gripper clamp, which is provided with a pair of opposite jaws (501d), defining a respective locking seat (501b) configured to receive the bone screw (3), and is provided with a through opening (501a) to receive the locking pin (502), which is arranged transversely with respect to a prevailing extension of said jaws (501d).

7. The locking device according to claim 1, wherein the coupling pin (504b) and the further coupling pin (506b) have respective pointed ends which, when the coupling pin (504b) and the further coupling pin (506b) are coupled with the support pin (202), are configured to create respective indentations in the support pin (202).

8. The locking device according to claim 1, wherein the coupling pin (504b) and the further coupling pin (506b) are made of steel and the support pin (202) is made of carbon fibre.

9. The locking device according to claim 1, wherein the through openings (503f) of the jaws (503d) of the coupling element (503) are arranged facing each other.

10. The locking device according to claim 1, wherein the fixing element (504, 505, 506) comprises a pair of clamping elements (505) and wherein each locking pin (502) comprises respective terminal ends (502a; 502b), each configured to receive a respective clamping element (505), the clamping elements (505) fixing an angular position of the locking element (501) with respect to the locking pin (502) and the locking device (5) with respect to the support pin (202).

11. The locking device according to claim 1, wherein the fixing element (504, 505, 506) comprises a pair of clamping elements (505) and wherein the locking pin (502) comprises respective terminal ends (502a; 502b), each configured to receive a respective clamping element (505), the clamping elements (505) fixing an angular position of the locking element (501) with respect to the locking pin (502) and the locking device (5) with respect to the support pin (202) and wherein the clamping elements (505) are configured to abut the locking element (501) on one side and the further stabilizing element (506) on the other, so as to clamp the locking element (501), the stabilizing element (504), the coupling element (502) and the further stabilizing element (506) to each other.

12. An external fixator (1) for bone fractures comprising at least two support units (2, 2') for removably supporting bone screws (3), wherein each support unit (2; 2') comprises:
  a pair of support bodies (201), which are curved;
  a single support pin (202) or a pair of support pins (202) fixed to one, or to both, of the support bodies (201);
  a pair of locking devices (5) of a bone screw (3) according to claim 1, which are both fixed to the single support pin (202) or, each to a respective support pin (202).

\* \* \* \* \*